United States Patent
Li et al.

(10) Patent No.: US 11,950,802 B2
(45) Date of Patent: Apr. 9, 2024

(54) DURA ELEVATING AND CUTTING APPARATUS

(71) Applicant: Dignity Health, San Francisco, CA (US)

(72) Inventors: Richard Li, San Francisco, CA (US); Alexander Dasilva, San Francisco, CA (US); Jake Xu, San Francisco, CA (US); Ambike Bhraguvanshi, San Francisco, CA (US); Michael Bohl, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 375 days.

(21) Appl. No.: 17/298,141

(22) PCT Filed: Nov. 26, 2019

(86) PCT No.: PCT/US2019/063227
§ 371 (c)(1),
(2) Date: May 28, 2021

(87) PCT Pub. No.: WO2020/112755
PCT Pub. Date: Jun. 4, 2020

(65) Prior Publication Data
US 2022/0015793 A1    Jan. 20, 2022

Related U.S. Application Data

(60) Provisional application No. 62/773,008, filed on Nov. 29, 2018.

(51) Int. Cl.
*A61B 17/3211* (2006.01)
*A61B 17/00* (2006.01)

(52) U.S. Cl.
CPC . *A61B 17/3211* (2013.01); *A61B 2017/00353* (2013.01); *A61B 2017/00389* (2013.01); *A61B 2017/32113* (2013.01)

(58) Field of Classification Search
CPC ...... A61B 17/3211; A61B 2017/32113; A61B 17/3213; B26B 29/02; B26B 29/025; A11B 90/10
USPC .................................. 606/167; 30/151–164
See application file for complete search history.

(56) References Cited

U.S. PATENT DOCUMENTS

| | | | | |
|---|---|---|---|---|
| 5,781,998 A | * | 7/1998 | Stamper | B26B 1/042 30/139 |
| 9,027,254 B1 | * | 5/2015 | Vodinh | A61B 17/3211 30/151 |
| 2002/0188309 A1 | | 12/2002 | Adelman et al. | |
| 2007/0276422 A1 | * | 11/2007 | Pooler | A61B 17/3211 606/167 |
| 2014/0345144 A1 | * | 11/2014 | Frazer | B26B 29/025 30/153 |
| 2015/0190165 A1 | | 7/2015 | Vodinh | |

(Continued)

OTHER PUBLICATIONS

Patent Cooperation Treaty, International Search Report and Written Opinion, International Application No. PCT/US2019/063227, dated Feb. 4, 2020, 11 pages.

*Primary Examiner* — Kathleen S Holwerda
*Assistant Examiner* — Serenity A Miller
(74) *Attorney, Agent, or Firm* — Polsinelli PC

(57) ABSTRACT

Various embodiments of a dural elevating and cutting apparatus and methods of use are disclosed herein.

16 Claims, 16 Drawing Sheets

(56) References Cited

U.S. PATENT DOCUMENTS

2017/0224371 A1\* 8/2017 Walzman ........... A61B 17/3211
2018/0242996 A1 8/2018 Hutchison et al.

\* cited by examiner

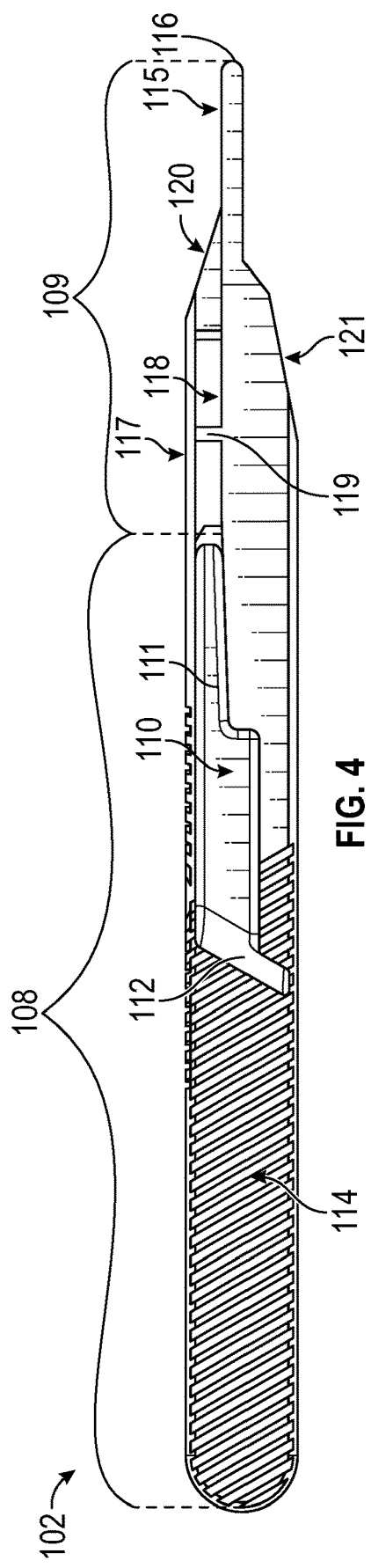
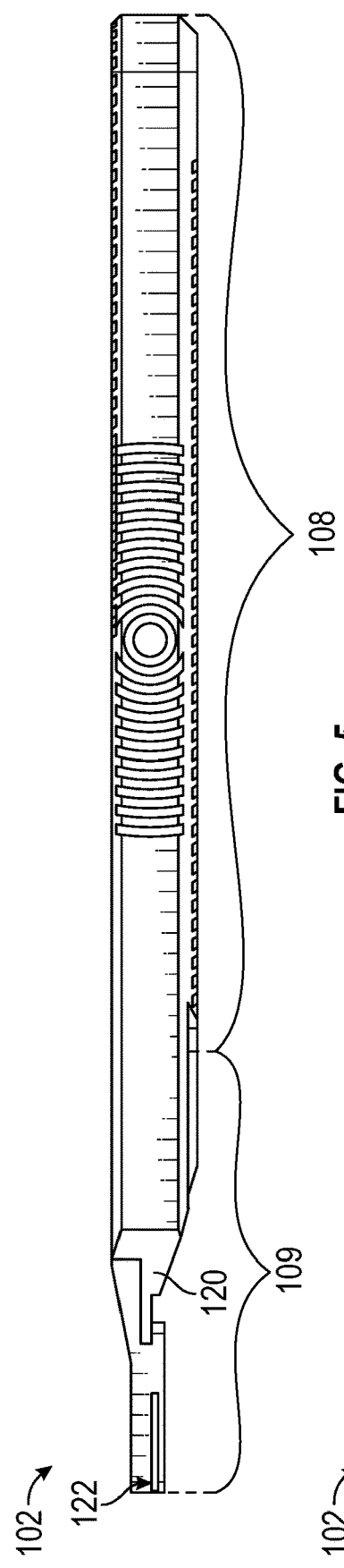
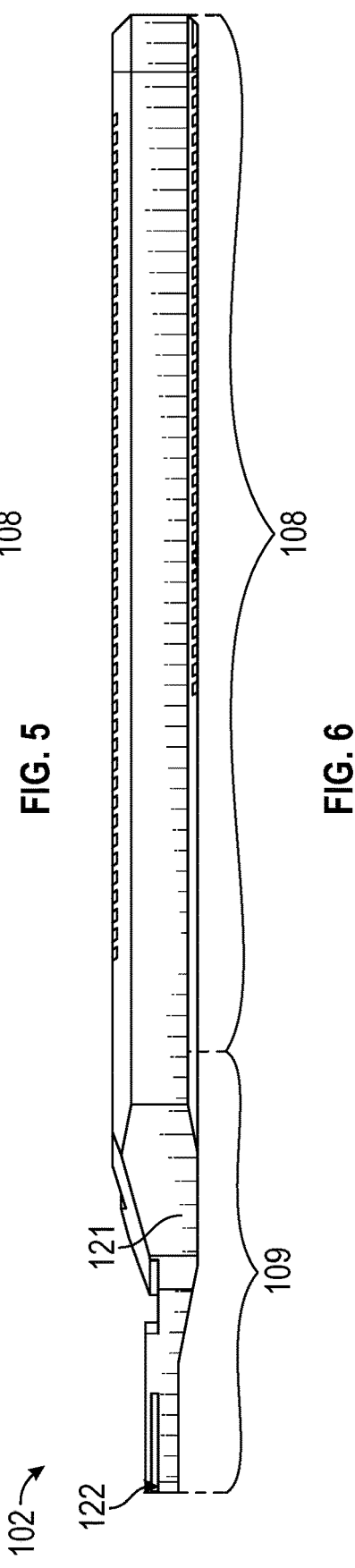
FIG. 4
FIG. 5
FIG. 6

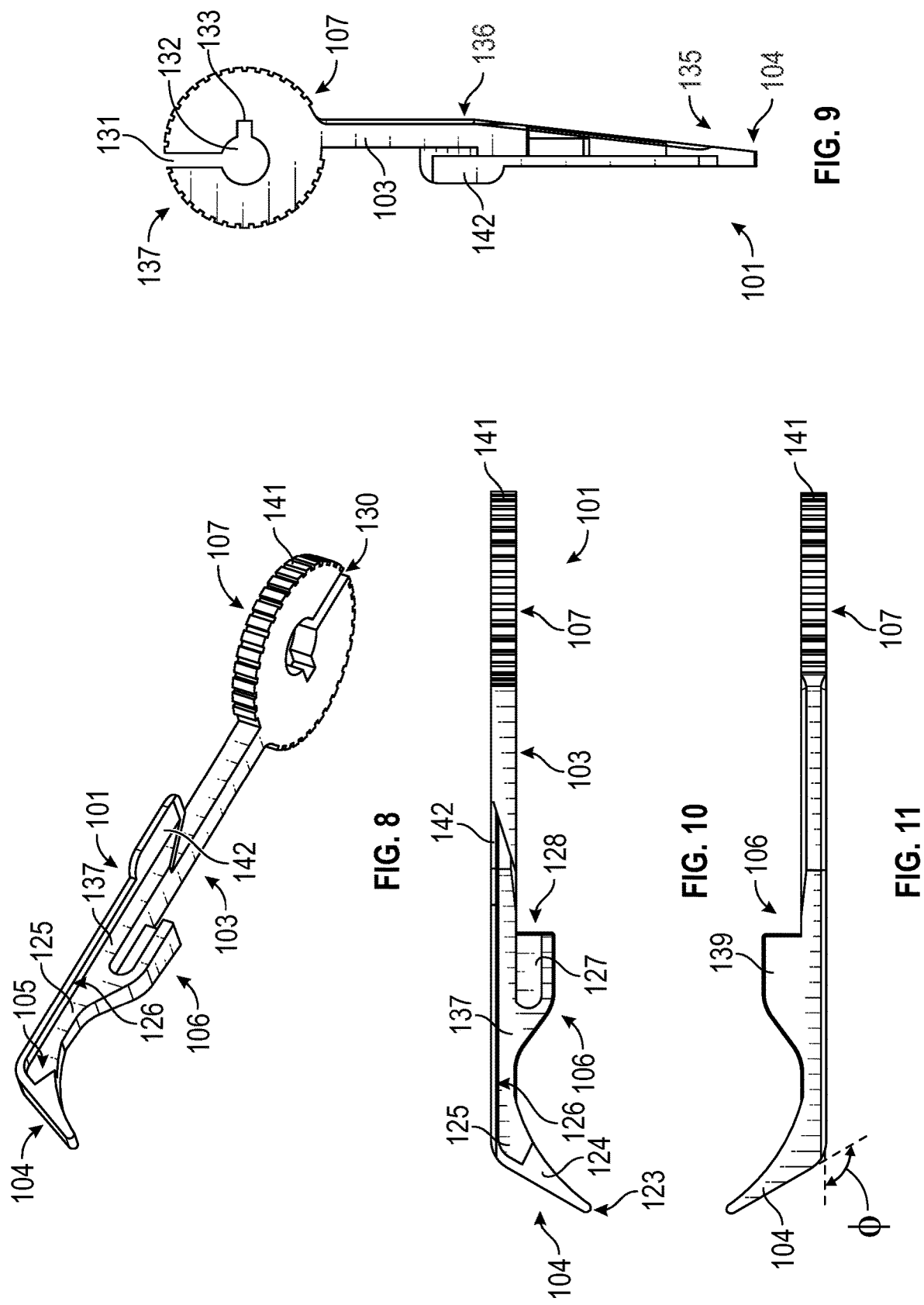

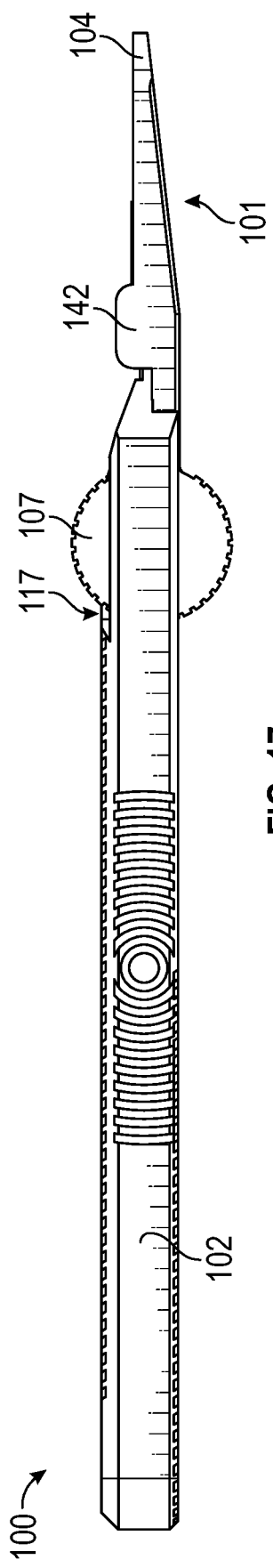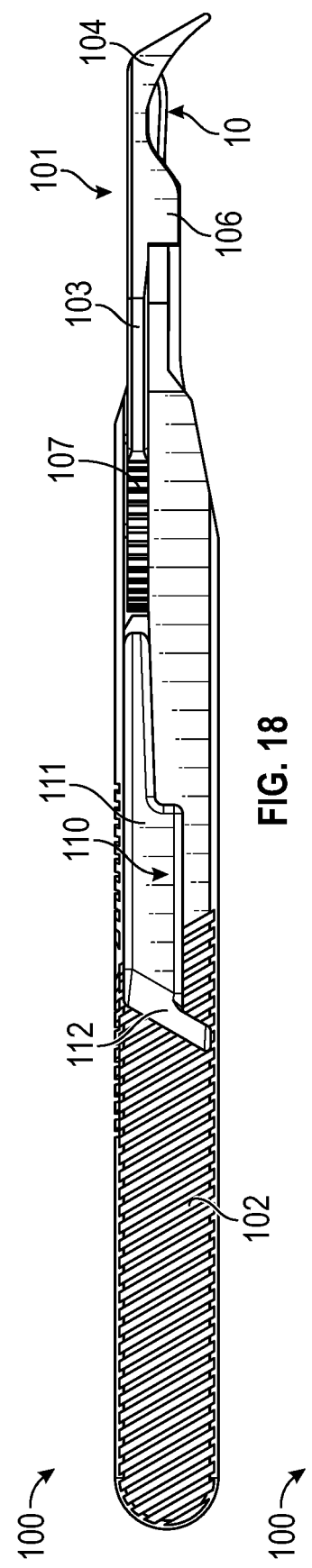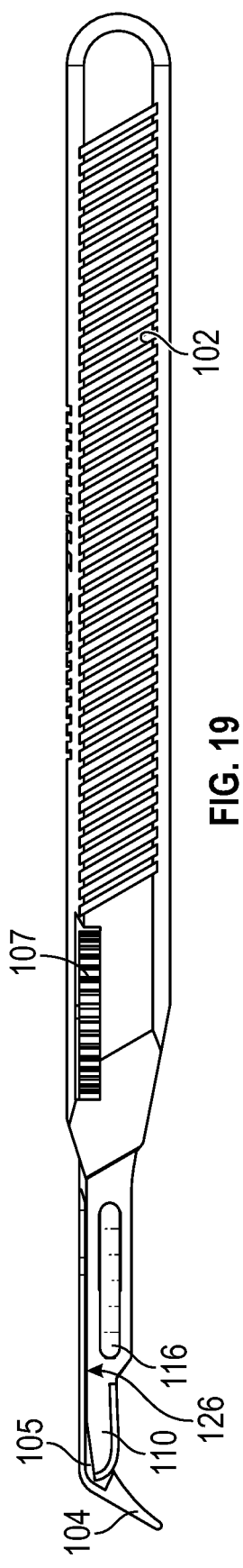
FIG. 17
FIG. 18
FIG. 19

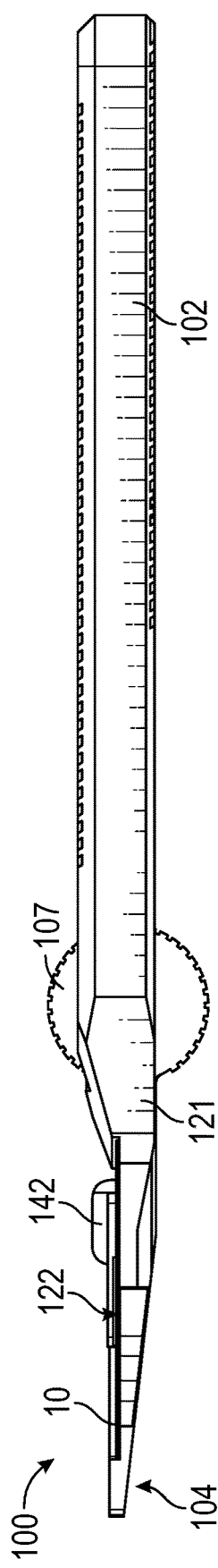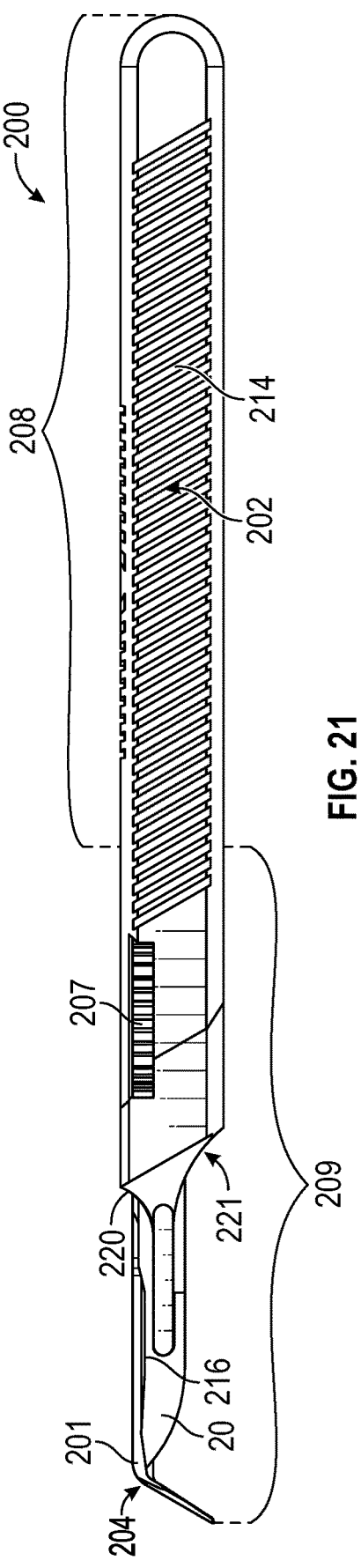
FIG. 20
FIG. 21

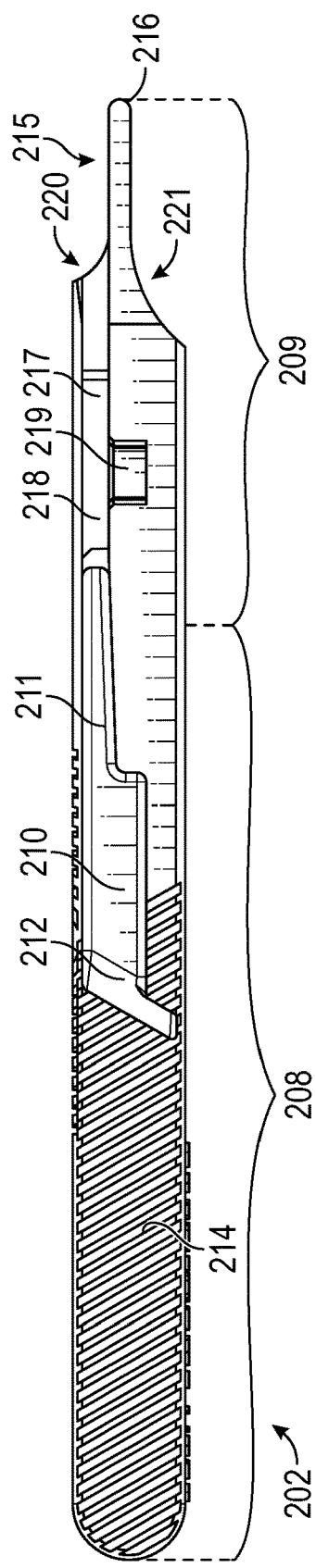
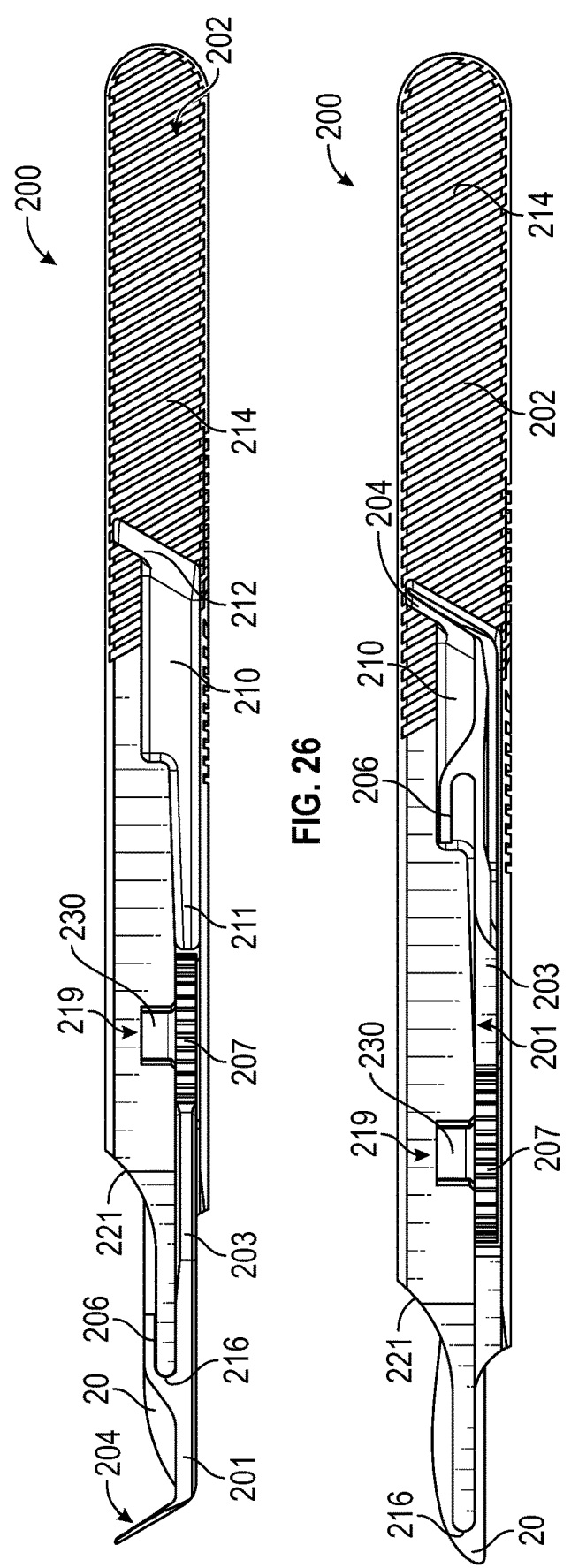
FIG. 25
FIG. 26
FIG. 27

DURA ELEVATING AND CUTTING APPARATUS

CROSS REFERENCE TO RELATED APPLICATIONS

This is a non-provisional application that claims benefit to U.S. provisional application Ser. No. 62/773,008 filed on Nov. 29, 2018, which is herein incorporated by reference in its entirety.

FIELD

The present disclosure generally relates to surgical devices, and in particular, to a surgical apparatus for lifting and incising dura mater during neurosurgery.

BACKGROUND

Neurosurgery often requires one or more incisions into the dura mater, a thin membrane encapsulating the brain underneath the skull. A tiny nick is created in the dura mater in order for a surgeon to insert a dural elevator and lift the dura mater away from the brain. This step allows a surgeon to hold the dura taut and away from the brain while cutting the dura and otherwise working within the space. Conventional technologies perform this task using separate tools to lift the dura and cut the dura, thereby requiring multiple hands to pass and hold very sharp blades while working in a small and delicate surgical space.

It is with these observations in mind, among others, that various aspects of the present disclosure were conceived and developed.

BRIEF DESCRIPTION OF THE DRAWINGS

FIG. 4 is a side view of the scalpel housing of FIG. 1 showing a shield storage slot for engagement with the shield;

FIG. 5 is a top view of the scalpel housing of FIG. 4;

FIG. 6 is a bottom view of the scalpel housing of FIG. 4;

FIG. 8 is a perspective view of the shield of FIG. 1;

FIG. 9 is a top view of the shield of FIG. 8;

FIG. 10 is a side view of the shield of FIG. 8 showing a blade shield and tip lock for engagement with the scalpel housing;

FIG. 11 is an opposite side view of the shield of FIG. 8;

FIG. 17 is a top view of the apparatus of FIG. 1 showing the blade shield engaged with a head portion of the scalpel housing;

FIG. 18 is a side view of the apparatus of FIG. 1 showing the blade shield engaged with the head portion of the scalpel housing;

FIG. 19 is an opposite side view of the apparatus of FIG. 1;

FIG. 20 is a bottom view of the apparatus of FIG. 1;

FIG. 21 is a side view of a second embodiment of a dura elevating and cutting apparatus including a scalpel housing and a shield shown in an engaged position;

FIG. 25 is a side view of the scalpel housing of FIG. 21;

FIG. 26 is an opposite side view of the apparatus of FIG. 21;

FIG. 27 is a side view of the apparatus of FIG. 21 shown in a recessed position;

Corresponding reference characters indicate corresponding elements among the view of the drawings. The headings used in the figures do not limit the scope of the claims.

DETAILED DESCRIPTION

Figure 1:
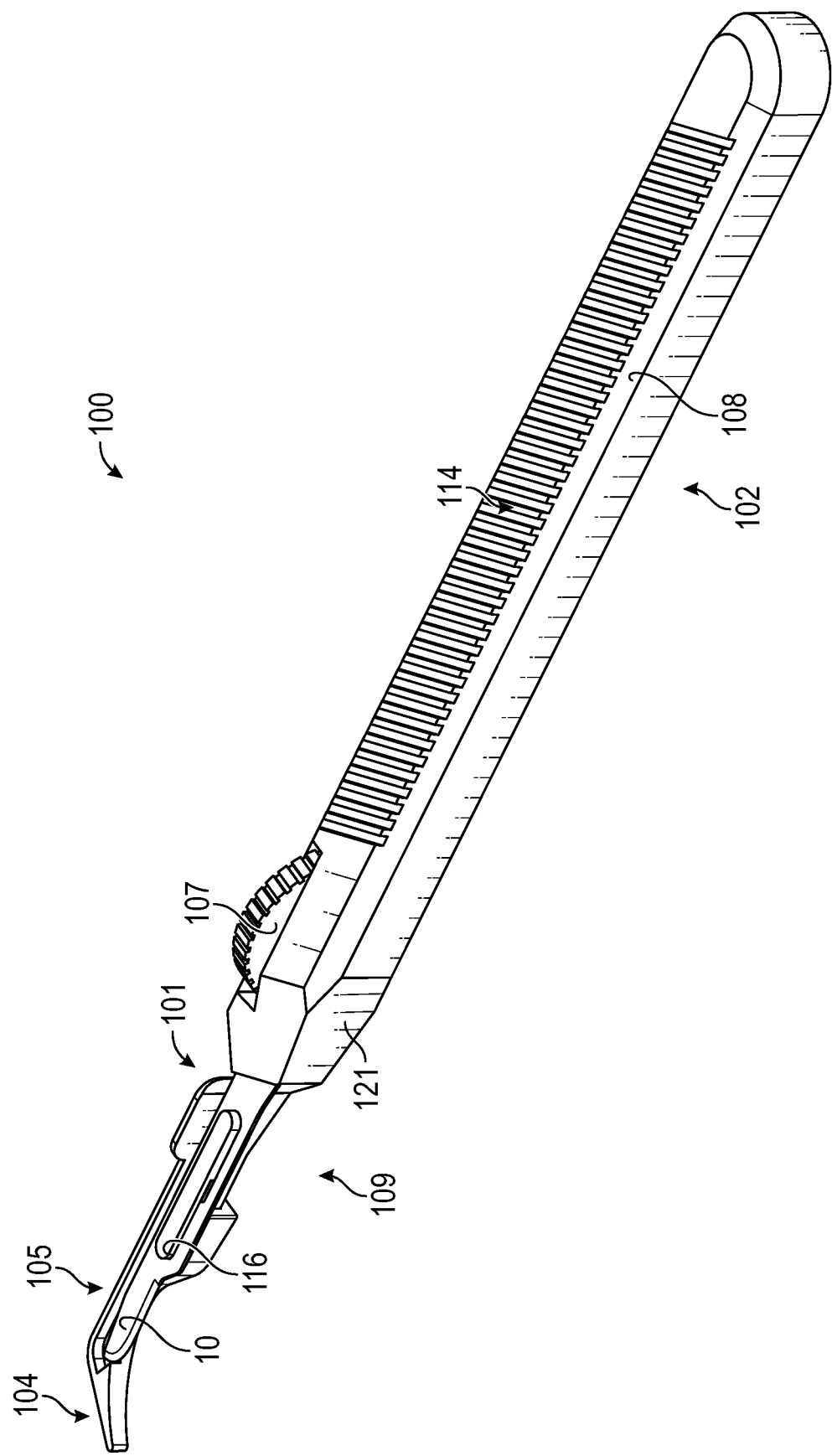
FIG. 1 is a perspective view of a first embodiment of a dura elevating and cutting apparatus showing a scalpel housing and a shield in an "engaged" position.
Figure 2:
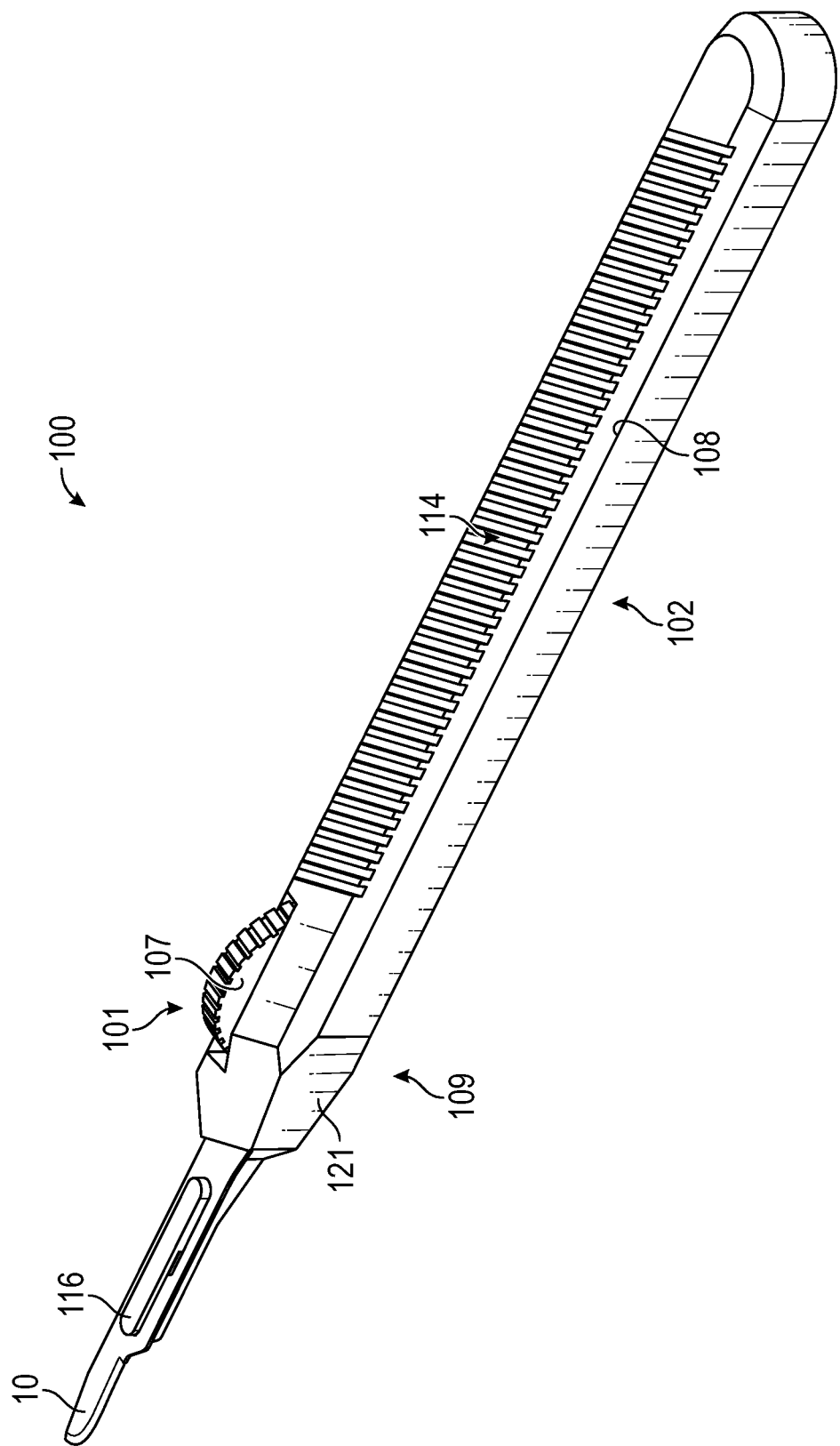
FIG. 2 is a perspective view of the present apparatus of FIG. 1 showing the shield in a "recessed" position.

Various embodiments of a dural elevating and cutting apparatus are disclosed herein. In some embodiments, the dural elevating and cutting apparatus includes a scalpel housing in engagement with a shield by a rotator defined at a proximal end of the shield. The scalpel housing includes a blade receptacle defined at a head portion of the scalpel housing for receiving and securing a standard scalpel blade. The shield further includes an elevator at a distal end of the shield configured for lifting dural tissue. The shield is operable for rotation between a recessed position in which the shield is disposed within the scalpel housing and an engaged position in which the shield covers the scalpel blade and is otherwise engaged with the head portion of the scalpel housing, thereby allowing a surgeon to use the scalpel blade installed within the scalpel housing to cut into tissue with the shield recessed or to use the shield to cover the blade and lift the dura mater to widen an incision in the dura mater. The surgeon can also cut the dura mater while in the engaged position by orienting the apparatus such that the dura mater is positioned between a cutting edge of the scalpel blade and the elevator and driving the apparatus along a direction the surgeon intends to cut. Referring to the drawings, embodiments of a dural elevating and cutting apparatus are illustrated and generally indicated as 100 in FIGS. 1-20, 200 in FIGS. 21-27, and 300 in FIGS. 28-30.

The dural elevating and cutting apparatus 100, shown in FIGS. 1-3 and 12-20 and referred to herein as "the apparatus", includes a scalpel housing 102 having a handle portion 108 configured for gripping by the surgeon and a head portion 109 configured to receive a scalpel blade 10 and a shield 101. The shield 101 defines a rotator 107 and a stem 103, where the stem 103 includes an elevator 104 and a blade shield 105 configured for elevating the dura mater and covering at least part of the scalpel blade 10. The rotator 107 engages with a rotator receptacle 117 defined by the head portion 109 of the scalpel housing 102 such that the shield 101 is operable for clockwise or counterclockwise rotation between a recessed position shown in FIG. 2 and an engaged position shown in FIG. 1. While in the recessed position, the stem 103 of the shield 101 engages with a shield storage slot 110 of the scalpel housing 102. Conversely, while in the engaged position, the blade shield 105 defined by the stem 103 engages with the head portion 109 of the scalpel housing 102 and the elevator 104 is positioned distal to the head portion 109.

As noted above, the scalpel housing 102 shown in FIGS. 4-7 includes the handle portion 108 and the head portion 109, wherein the head portion 109 is configured to receive the scalpel blade 10 and the shield 101. The head portion 109 defines an elongated tip 116 and a blade receptacle 122 configured for engagement with the scalpel blade 10 at a distal end 115 of the scalpel housing 102. An upper angled surface 120 and a lower surface 121 are also defined along the head portion 109. In addition, the head portion 109 further defines a rotator receptacle 117 located between the handle 108 and the upper angled surface 120, wherein the rotator receptacle 117 is configured for engagement with the rotator 107 of the shield 101. The handle 108 includes a gripping portion 114 and a shield storage slot 110 defined along a handle surface 113 of the handle 108. The shield storage slot 110 defines a channel portion 111 and a tip slot 112 for receiving the respective stem 103 and elevator 104 of the shield 101 when in the recessed position. In some embodiments, the tip 116 and blade receptacle 122 defined at the distal end 115 of the scalpel housing 102 are configured for engagement with most standard disposable scalpel blades 10. In some embodiments such as the embodiment of FIG. 4, the rotator receptacle 117 includes a horizontal slot 118 defined through the head portion 109. A post 119 is formed within the horizontal slot 118 of the rotator receptacle 117 for engagement with the rotator 107 of the shield 101, a mechanism which will be described in greater detail below.

Figure 12C:
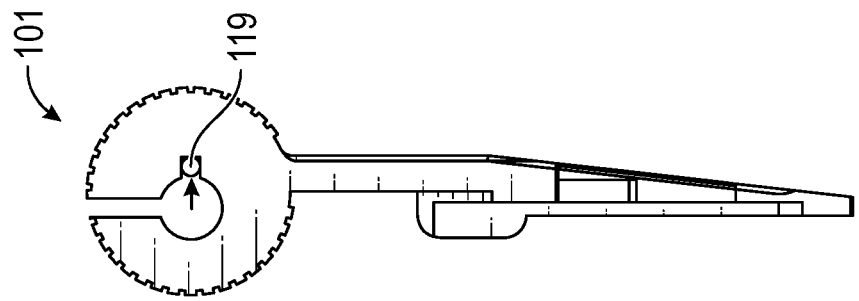
FIG. 12C is a top view of the shield and post of FIG. 12A showing the post engaged within a latitudinal portion of the shield.
Figure 12B:
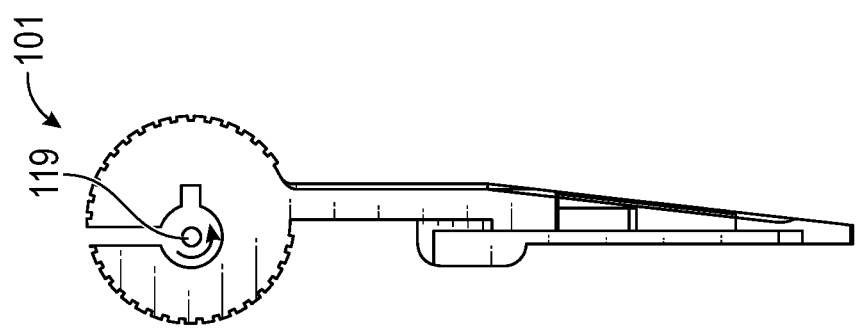
FIG. 12B is a top view of the shield and post of FIG. 12A showing the post engaged within a circular portion of the shield.
Figure 12A:
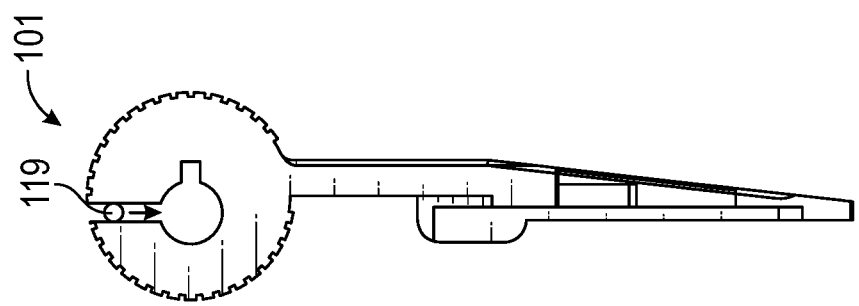
FIG. 12A is a top view of the shield of FIG. 9 showing a post of a rotator receptacle partially engaged within an longitudinal portion of the shield.
Figure 13:
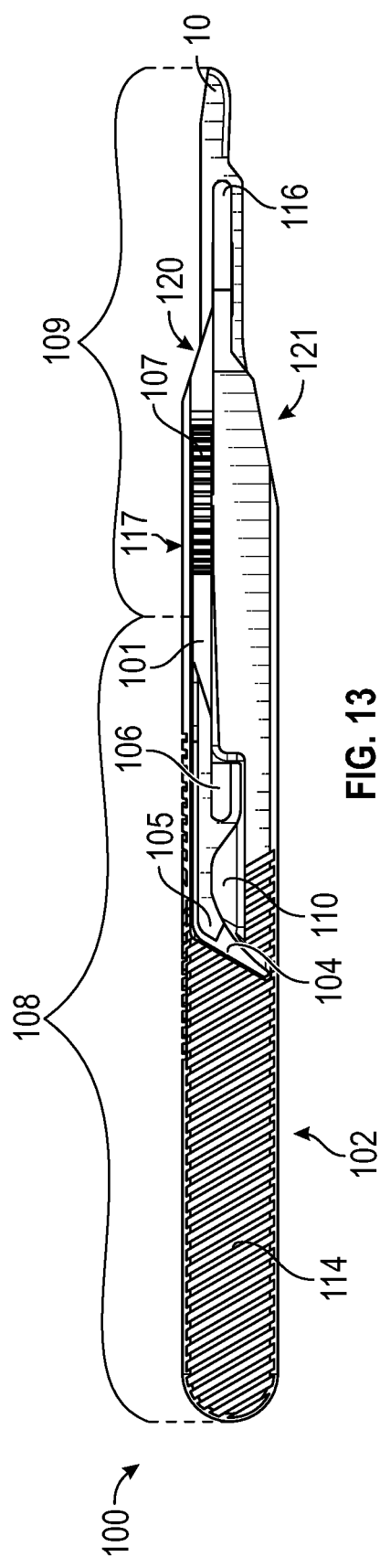
FIG. 13 is a side view of the apparatus of FIG. 2 showing the shield engaged inside the shield storage slot.
Figure 14:
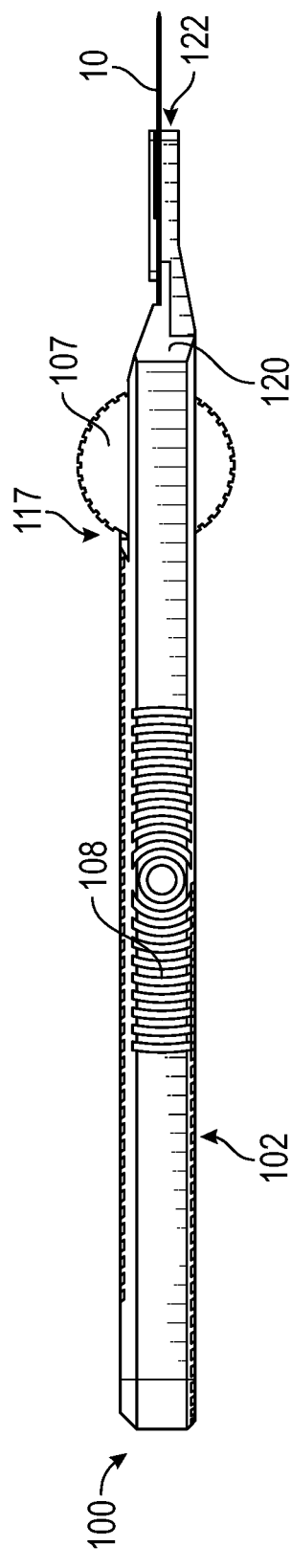
FIG. 14 is a top view of the apparatus of FIG. 2.
Figure 15:
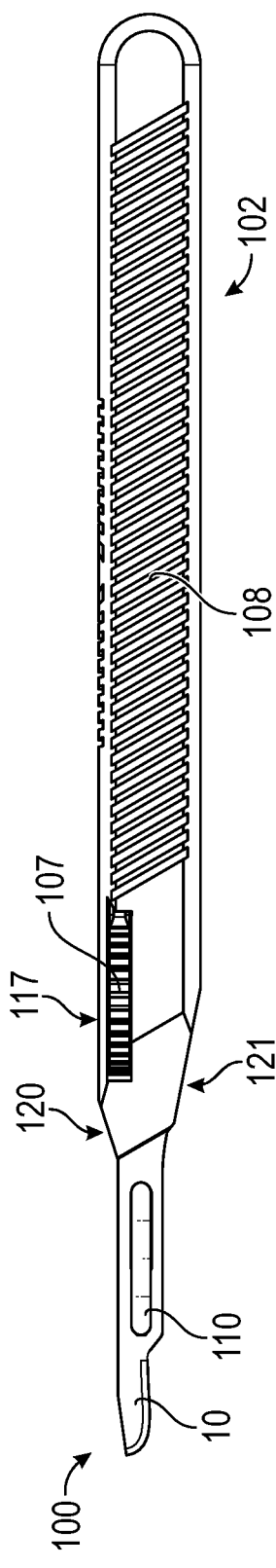
FIG. 15 is an opposite side view of the apparatus of FIG. 2.

FIGS. 8-11 illustrate the shield 101 of the apparatus 100 including the stem 103, the rotator 107 defined at a proximal end 134 of the stem 103, and the elevator defined at a distal end 135 of the stem 103. Furthermore, the blade shield 105 and the tip lock 106 are defined along a midsection 136 of the stem 103 for engagement with the scalpel blade 10 and tip 116 of the scalpel housing 102. The rotator 107 is a circular-shaped structure defined at the proximal end 134 of the stem 103 and configured for engagement with the rotator receptacle 117 of the scalpel housing 102. The rotator 107 further defines a pathway 130, shown in FIGS. 9 and 12A-C, where the pathway 130 forms a longitudinal portion 131 in communication with a circular portion 132 and a latitudinal portion 133, where the opening of the longitudinal portion 131 is defined along the peripheral edge 141 of the rotator 107. This configuration of the longitudinal portion 131, circular portion 132 and latitudinal portion 133 allows for insertion of the rotator 107 into the horizontal slot 118 of the rotator receptacle 117 such that the longitudinal portion 131 receives the post 119 (shown in FIG. 12A) and the rotator 107 can be moved relative to the post 119 such that the post 119 is moved into the circular portion 132, as shown in FIG. 12B. In this position, the rotator 107 may be manually rotated in a clockwise or counterclockwise direction A such that the stem 103 of the shield 101 is engaged within the shield storage slot 110 of the scalpel housing 102 in the recessed position of FIG. 2. The rotator 107 may also be manually rotated in an opposite counterclockwise or clockwise direction B such that the blade shield 105 of the shield 101 is oriented towards the head portion 109 of the scalpel housing 102 in the engaged position of FIG. 1. While the blade shield 105 is oriented towards the head portion 109, the shield 101 may then be driven in a lateral direction relative to the scalpel housing 102 such that the post 119 slides out of the circular portion 132 and then engages the latitudinal portion 133, as shown in FIG. 12C.

The blade shield 105 of the shield 101 further defines an indentation 125 along a lateral side 137 of the stem 103 for engagement with the scalpel blade 10 when in the engaged position. When driving the shield 101 in the lateral direction such that the post 119 engages the latitudinal portion 133 of the pathway 130, the indentation 125 defined along the stem 103 also engages with the scalpel blade 10 as shown in FIG. 20. The blade shield 105 further defines a brim 126 directly above the indentation 125 in a direction of elongation of the shield 101 for engagement with the upper angled surface 120 while in the engaged position, as shown in FIG. 17. A tab 142 is defined at a proximal end of the brim 126 to provide a surface for a surgeon to place their finger over the blade receptacle 122 for added stability in the hand. In some embodiments, the tab 142 may include textured grooves (not shown) along an upper surface of the tab 142 for haptic feedback. The blade shield 105 also defines a tip lock 106 for engagement with the tip 116 of the head portion 109 of the scalpel housing 102. In some embodiments, the tip lock 106 includes an elongated semicircular recess 128 configured for engagement with the tip 116. As shown in FIGS. 10, 11, and 18, some embodiments of the tip lock 106 include a tip lock wall 127 defined along a lateral edge 139 of the tip lock 106 for added stability.

The shield 101 further includes the elevator 104 defined at the distal end 135 of the stem 103. When in the engaged position, the elevator 104 extends beyond the blade 10 for lifting the dura mater away from the brain. The elevator 104 terminates at a point 123, where the point 123 may include a dulled edge so as to gently lift the dura mater without puncturing or otherwise unintentionally damaging tissue. In some embodiments, the elevator 104 includes an elevator ramp 124 to further shield the brain tissue and dura mater from the blade 10. As shown in FIGS. 10 and 11, the elevator 104 creates an obtuse angle φ relative to the direction of elongation of the shield 102. The obtuse angle φ formed by the elevator 104 in some embodiments may be 110°, but the obtuse angle φ may vary depending on the surgeon's preference.

Figure 3:
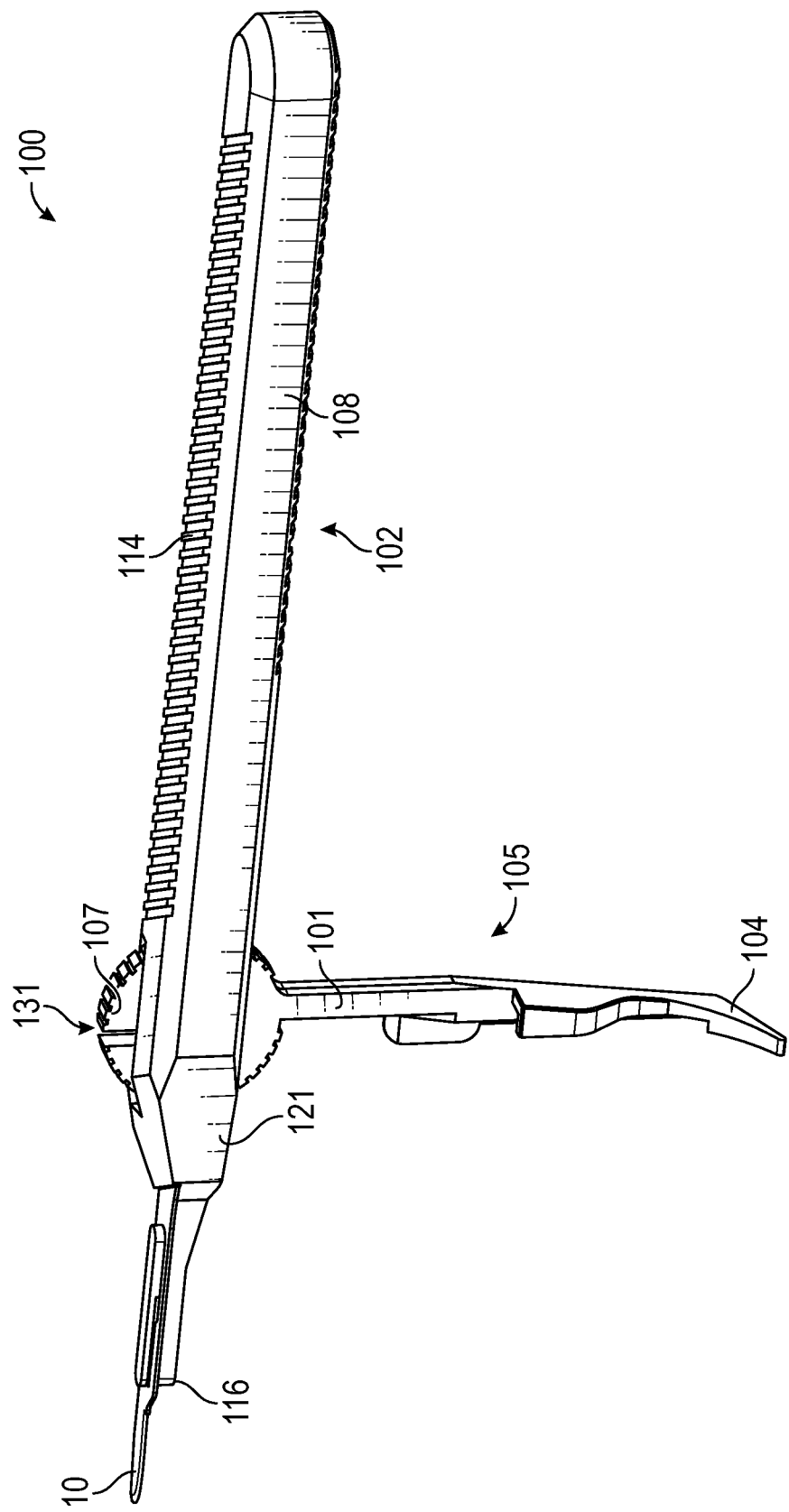
FIG. 3 is a perspective view of the present apparatus of FIG. 1 showing the shield between the engaged and recessed position.
Figure 7:
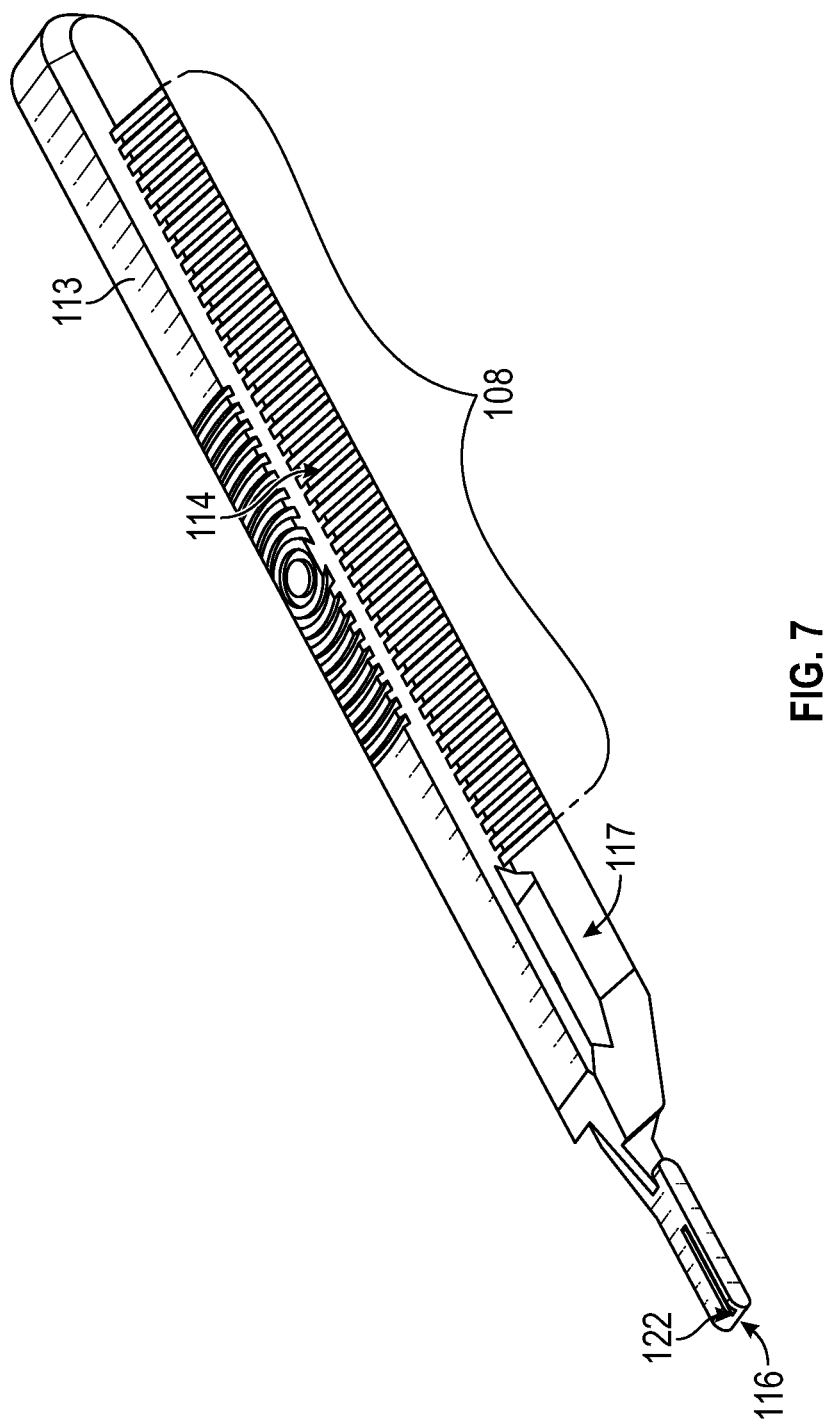
FIG. 7 is a top perspective view of the scalpel housing of FIG. 4.
Figure 16:
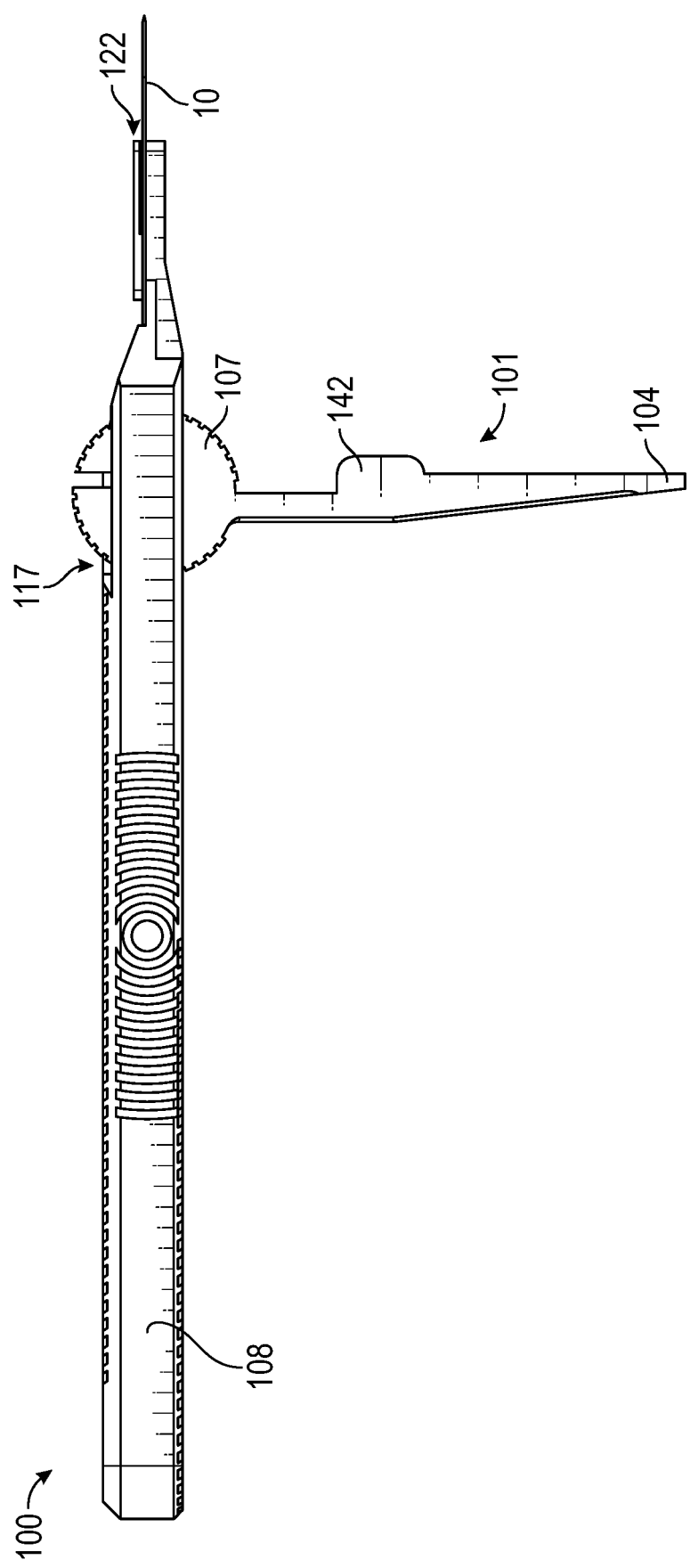
FIG. 16 is a top view of the apparatus of FIG. 3.

FIGS. 1 and 17-20 illustrate the apparatus 100 having the blade 10 engaged within the indentation 125 of the blade shield 105 and the elevator 104 located in distal relation to the tip 116 when in the engaged position. Conversely, FIGS. 2 and 13-15 illustrate the apparatus 100 having the shield 101 engaged within the shield storage slot 110 when in the recessed position with the blade 10 exposed for contact with tissue. As discussed above, the shield 101 is operable for rotation between the engaged and recessed positions. FIGS. 3 and 16 illustrate the apparatus 100 between the engaged and recessed positions having the rotator 107 engaged within the rotator receptacle 117 and with the distal end 135 of the shield 101 extending laterally along a direction of elongation of the scalpel housing 102, rather than engaged within the shield storage slot 110 as in the recessed position or engaged with the head portion 109 of the scalpel housing 102 as in the engaged position.

In one method of use of the apparatus 100, a preliminary incision is made using the blade 10 while the apparatus 100 is in the recessed position. The shield 101 is then moved into the engaged position such that the elevator 104 extends distally to the tip 116 of the scalpel housing 102. The elevator 104 is then inserted into the preliminary incision and may be used to lift the dura mater away from the brain. To expose the blade 10 for cutting purposes, the shield 101 can be rotated away from the engaged position and back to the recessed position such that the shield 101 is seated within the shield storage slot 110 of the scalpel housing 102. The surgeon can also cut the dura mater while in the engaged position by orienting the apparatus 100 such that the dura mater is positioned between a cutting edge of the scalpel blade 10 and the ramp 124 of the elevator 104 and driving the apparatus 100 along a direction the surgeon intends to cut.

FIGS. 25-27 illustrate a second embodiment of the dural elevating and cutting apparatus designated 200, having a scalpel housing 202 and including a handle portion 208 and a head portion 209 configured to receive a scalpel blade 20 and a shield 201. The shield 201 defines a rotator 207 and a stem 203, where the stem 203 includes an elevator 204 and a blade shield 205 for elevating the dura mater and covering at least part of the scalpel blade 20. The rotator 207 engages with a rotator receptacle 217 defined by the head portion 209 of the scalpel housing 202 such that the shield 201 is operable for clockwise or counterclockwise rotation between a recessed position shown in FIG. 27 and an engaged position shown in FIG. 25. While in the recessed position, the stem 203 of the shield 201 engages with a shield storage slot 210 of the scalpel housing 202. Conversely, while in the engaged position, the blade shield 205 defined by the stem 203 engages with the head portion 209 of the scalpel housing 202 and the elevator 204 is located distal to the head portion 209.

As noted above, the scalpel housing 202 shown in FIG. 21 includes the handle portion 208 and the head portion 209, where the head portion 209 is configured to receive the scalpel blade 20 and the shield 201. The head portion 209 defines an elongated tip 216 and a blade receptacle 222 configured for engagement with the scalpel blade 20 at a distal end 215 of the scalpel housing 202. An upper angled surface 220 and a lower surface 221 are also defined along the head portion 209 and the upper angled surface 220 is configured for engagement with the shield 201. Lastly, the head portion 209 further defines a rotator receptacle 217 located between the handle 208 and the upper angled surface 220, wherein the rotator receptacle 217 is configured for engagement with the rotator 207 of the shield 201. The handle 208 includes a gripping portion 214 and a shield storage slot 210 defined along a handle surface 213 of the handle 208. The shield storage slot 210 defines a channel portion 211 and a tip slot 212 for receiving the respective stem 203 and elevator 204 of the shield 201 when in the recessed position. In some embodiments, the tip 216 and blade receptacle 222 defined at the distal end 215 of the scalpel housing 202 are configured for engagement with most standard disposable scalpel blades 20. In some embodiments such as the embodiment of FIG. 21, the rotator receptacle 217 includes a horizontal slot 218 defined through the head portion 209. A well 219 is formed within the horizontal slot 218 of the rotator receptacle 217 for engagement with the rotator 207 of the shield 201, a mechanism which will be described in greater detail below.

Figure 22:
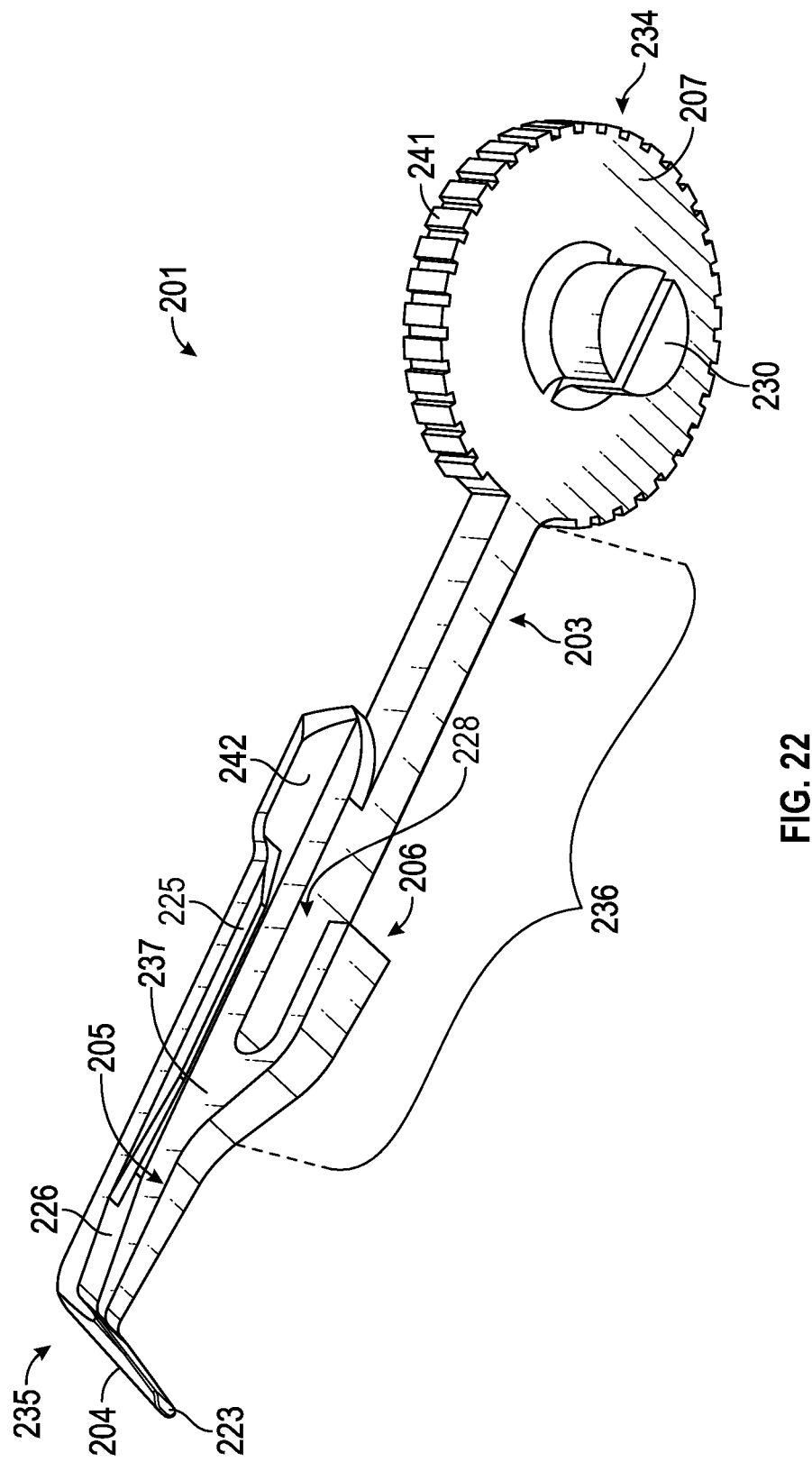
FIG. 22 is a perspective view of the shield of the apparatus of FIG. 21.
Figure 23:
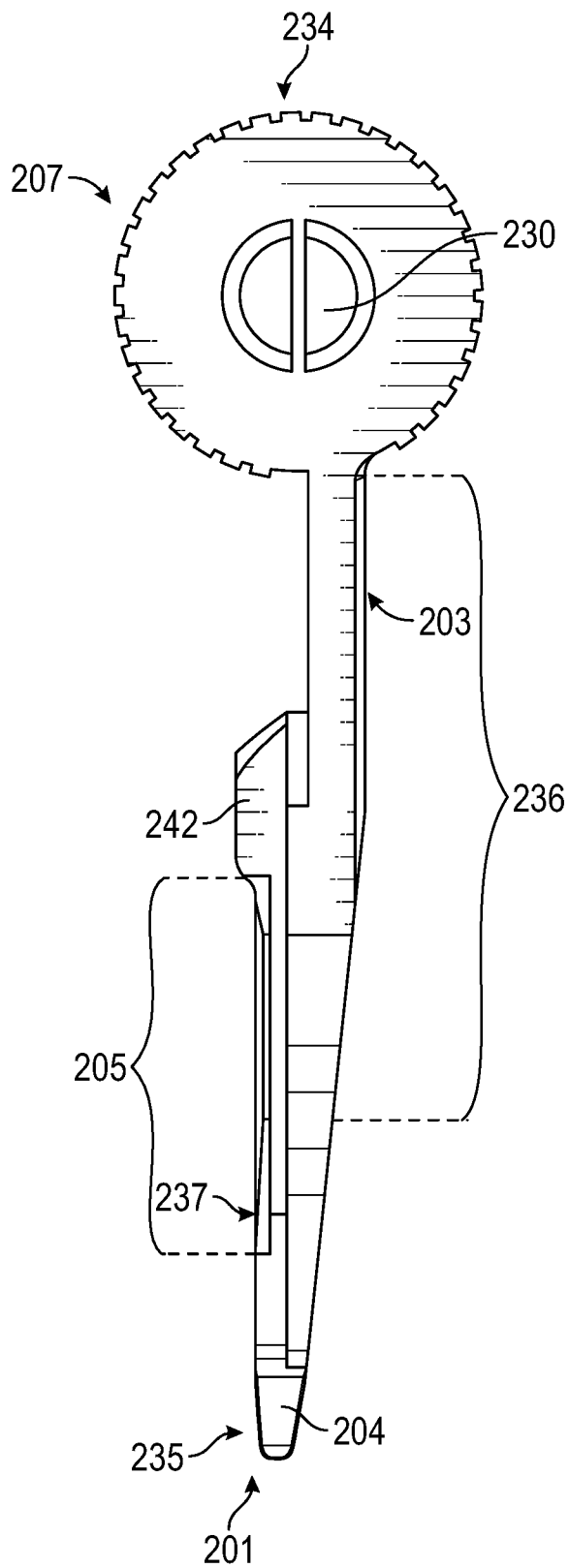
FIG. 23 is a top view of the shield of FIG. 21.
Figure 24:
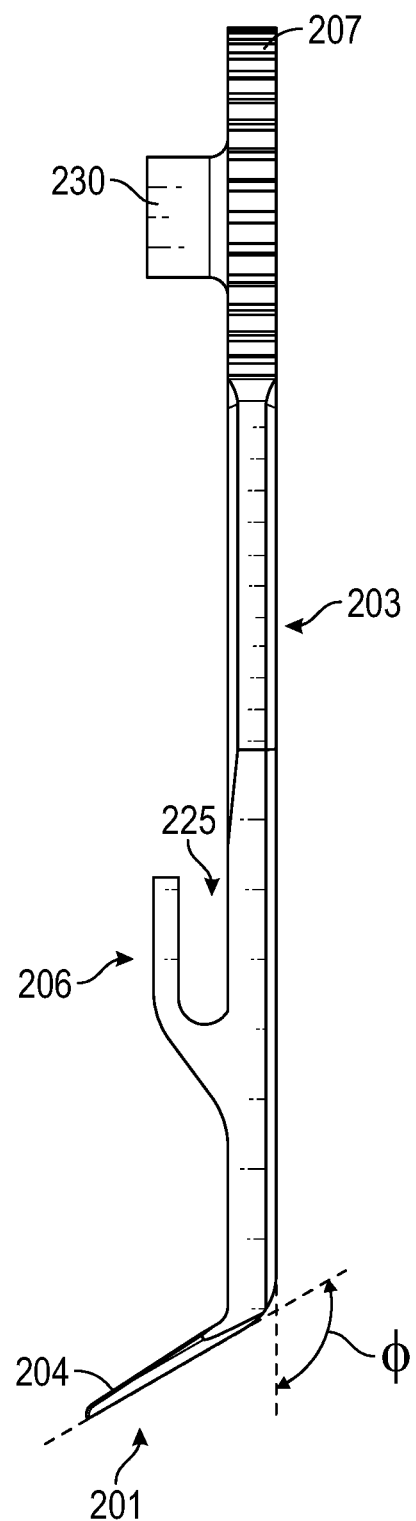
FIG. 24 is a side view of the shield of FIG. 21.

Similar to the embodiment of the apparatus 100, FIGS. 22-24 illustrate the shield 201 of the apparatus 200 including the stem 203, the rotator 207 defined at a proximal end 234 of the stem 203 and the elevator defined at a distal end 235 of the stem 203. Furthermore, the blade shield 205 and the tip lock 206 are defined along a midsection 236 of the stem 203 for engagement with the scalpel blade 20 and tip 216 of the scalpel housing 202. The rotator 207 is a circular-shaped structure defined at the proximal end 234 of the stem 203 and configured for engagement with the rotator receptacle 217 of the scalpel housing 202. The rotator 207 further defines a rotator post 230 protruding from a face 207A of the rotator 207. The rotator 207 is inserted into the horizontal slot 218 of the rotator receptacle 217 such that the well 219 receives the rotator post 230 and the rotator 207 can be rotated within the rotator post 230. In this position, the rotator 207 may be manually rotated in a clockwise or counterclockwise direction A such that the stem 203 of the shield 201 is engaged within the shield storage slot 210 of the scalpel housing 202 in the recessed position of FIG. 27. The rotator 207 may also be manually rotated in an opposite counterclockwise or clockwise direction B such that the blade shield 205 of the shield 201 is oriented towards the head portion 209 of the scalpel housing 202 in the engaged position of FIGS. 25-26.

The blade shield 205 of the shield 201 further defines an indentation 225 along a lateral side 237 of the stem 203 for engagement with the scalpel blade 20 when in the engaged position. When in the engaged position, the indentation 225 defined along the stem 203 also engages with the scalpel blade 20 as shown in FIG. 20. The blade shield 205 further defines a brim 226 directly above the indentation 225 along a direction of elongation of the shield 201 for engagement with the upper angled surface 220 while in the engaged position, as shown in FIGS. 22, 25 and 26. Similar to the previous embodiment of the apparatus 100, a tab 242 is defined at a proximal end of the brim 226 to provide a surface for a surgeon to place their finger over the blade receptacle 222 for added stability within the hand. In some embodiments, the tab 242 may include textured grooves (not shown) along an upper surface of the tab 242 for haptic feedback. The blade shield 205 also defines a tip lock 206 for engagement with the tip 216 of the head portion 209 of the scalpel housing 202. In some embodiments, the tip lock 206 includes an elongated semicircular recess 228 configured for engagement with the tip 216. Unlike the tip lock 106 of the previous embodiment of the apparatus 100, some embodiments such as the embodiment shown in FIGS. 22-24 do not include a tip lock wall.

The shield 201 further includes the elevator 204 defined at the distal end 235 of the stem 203. When in the engaged position, the elevator 204 extends beyond the blade 20 for lifting the dura mater away from the brain. The elevator 204 terminates at a point 223, where the point 223 may include a dulled edge so as to gently lift the dura mater without puncturing or otherwise unintentionally damaging tissue. As shown in FIG. 24, the elevator 204 creates an obtuse angle φ relative to the direction of elongation of the shield 202. The obtuse angle φ may be 110°, but the obtuse angle φ may vary between embodiments depending on the surgeon's preference.

FIGS. 25 and 26 illustrate the apparatus 200 having the blade 20 engaged within the indentation 225 of the blade shield 205 and the elevator 204 located in distal relation to the tip 216 when in the engaged position. Conversely, FIG. 27 illustrates the apparatus 200 having the shield 201 engaged within the shield storage slot 210 when in the recessed position with the blade 20 exposed for contact with tissue. As discussed above, the shield 201 is operable for rotation between the engaged and recessed positions. In one method of use of the apparatus 200, a preliminary incision is made using the blade 20 while the apparatus 200 is in the recessed position. The shield 201 is then moved into the engaged position such that the elevator 204 extends distal to the tip 216 of the scalpel housing 202. The elevator 204 is then inserted into the preliminary incision and may be used to lift the dura mater away from the brain. To expose the blade 20 for cutting purposes, the shield 201 can be rotated away from the engaged position and back to the recessed position such that the shield 201 is seated within the shield storage slot 210 of the scalpel housing 202. The surgeon can also cut the dura mater while in the engaged position by orienting the apparatus 200 such that the dura mater is positioned between a cutting edge of the scalpel blade 20 and the elevator 204 and driving the apparatus 200 along a direction the surgeon intends to cut.

Figure 28:
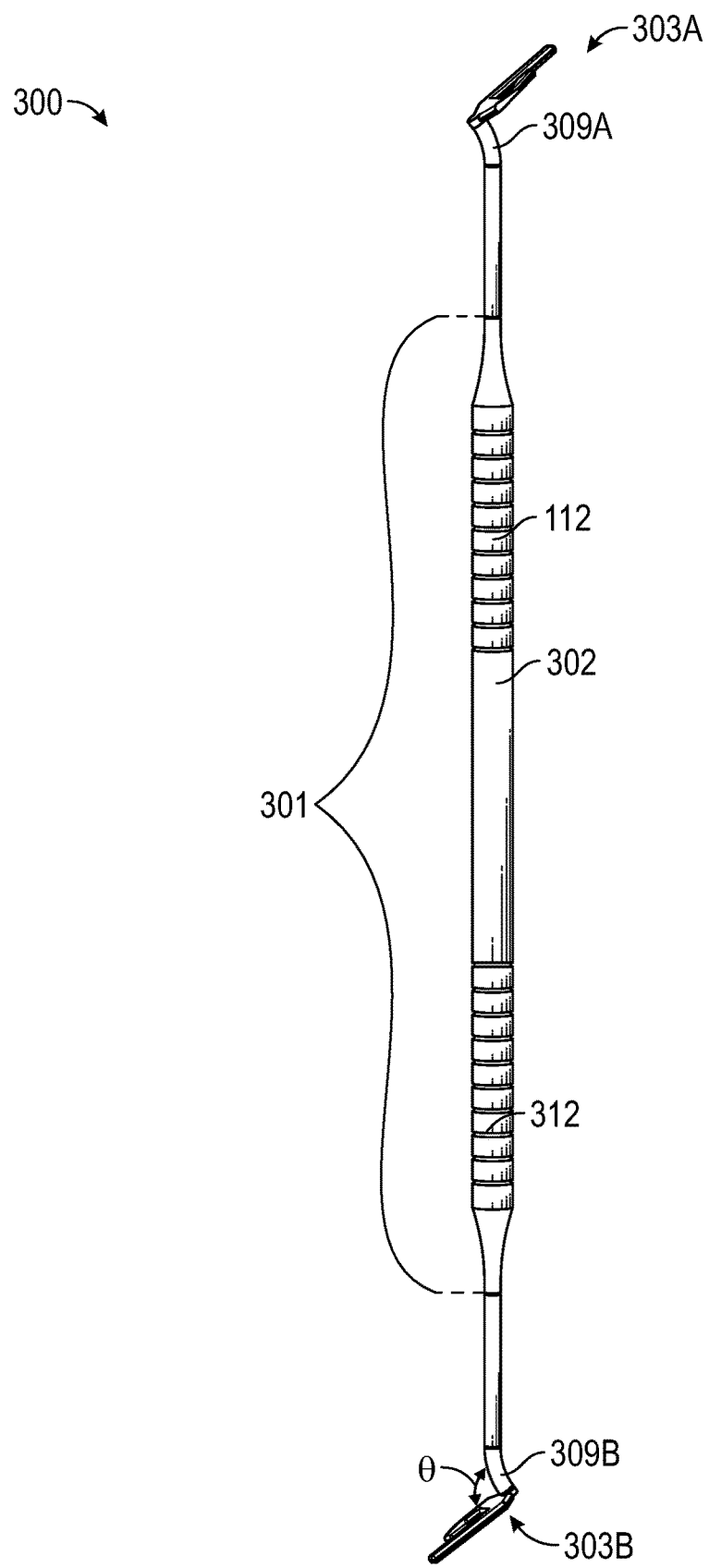
FIG. 28 is a perspective view of a third embodiment of a dura elevating and cutting apparatus including two heads.
Figure 29A:
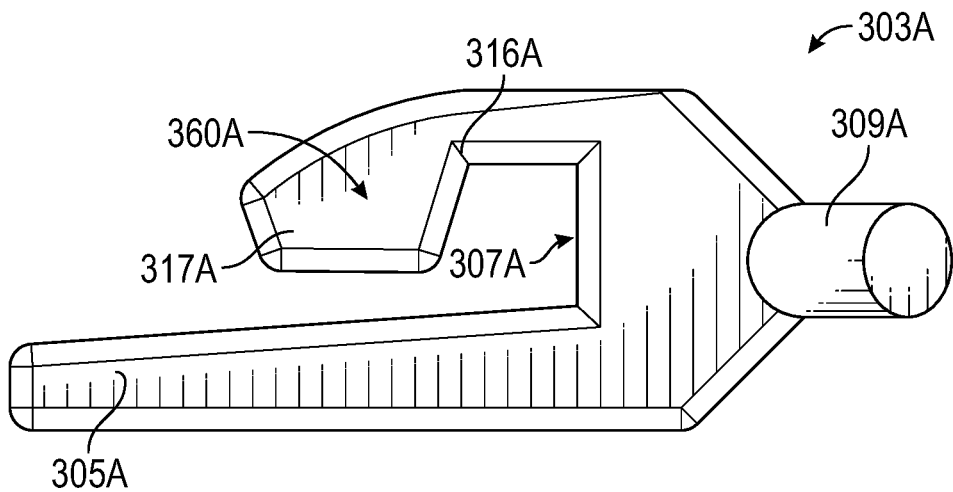
FIG. 29A is a top view of a first head portion of the apparatus of FIG. 28.
Figure 29B:
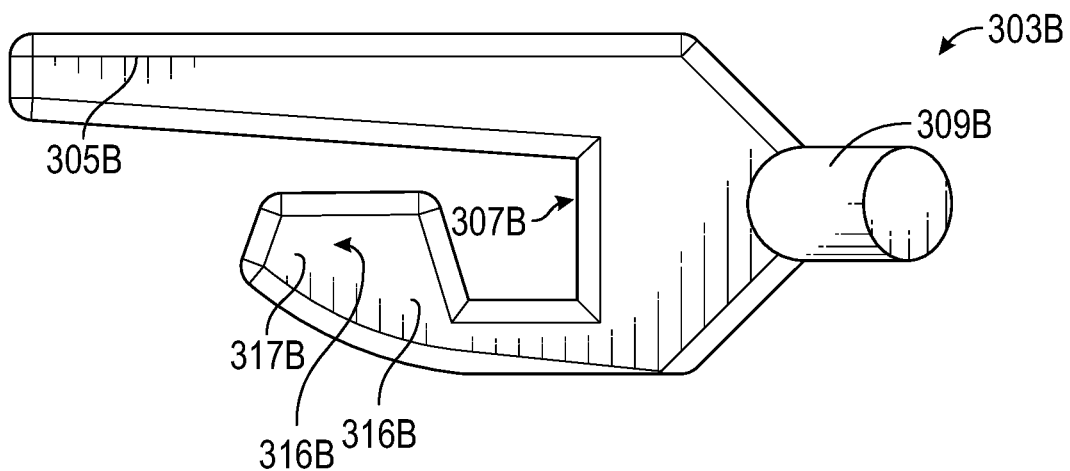
FIG. 29B is a top view of a second head portion of the apparatus of FIG. 28.
Figure 30:
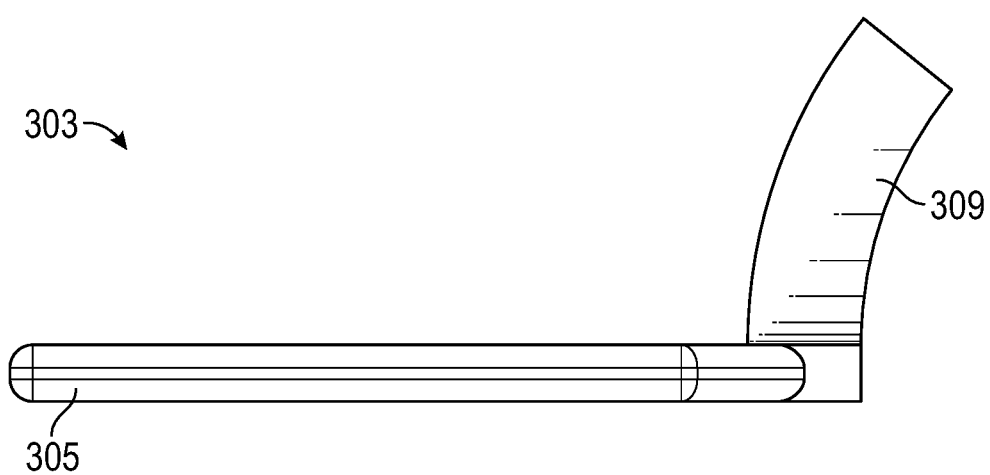
FIG. 30 is a side view of a head portion of the apparatus of FIG. 28 featuring a curved neck.

Referring to FIGS. 28-30 a third embodiment of a dural elevating and cutting apparatus, designated 300, may include an elongated body 301 comprising a handle 302 and each end of the elongated body 301 terminating in a head portion 303. Each head portion 303A (or 303B) includes an elevator 305A (or 305B) and a blade shield 306A (or 306B), both extending laterally from a direction of elongation of the elongated body 301. In some embodiments, a blade receptacle 307A (or 307B) is formed between the elevator 305A (or 305B) and the blade shield 306A (or 306B) and is configured to receive a scalpel blade 30. In some embodiments, the scalpel blade 30 is integral to the head portion 303 and cannot be removed.

As shown in FIGS. 28 and 29A-29B, the heads 303A and 303B are mirrored such that the apparatus 300 can be used by a left-handed surgeon or a right-handed surgeon without having to equip an exclusively left or right handed tool. In addition, FIG. 29A illustrates the blade shield 306A defining an elbow 316A and an inner arm 317A for shielding brain tissue from contacting the blade 30 while lifting or cutting the dura mater. Similarly, FIG. 29B illustrates the blade shield 306B defining an elbow 316B and an inner arm 317B. In some embodiments, the length of the elevator 305 is greater than the length of the blade shield 306. As shown in FIGS. 28 and 30, each of the heads 303A-B is defined at each respective terminal end of the elongated body 301 by a curved neck 309. Due to the curvature of the neck 309, the elevator 305 defines an obtuse angle θ relative to the direction of elongation of the elongated body 301. In some embodiments, each of the heads 303A and 303B are detachable from the handle 302 of the elongated body 301 by any suitable engagement. In some embodiments, the handle 302 includes a gripping portion 312 defined along a surface of the handle 302.

In one method of use, the apparatus 300 can be used to lift the dura mater away from the brain and cut the dura mater. For example, one of the elevators 305 may be inserted through a preliminary incision in the dura mater with the elevator 305 pointing in a direction that a surgeon wishes to cut along. The surgeon can then lift the dura mater away from the brain using the elevator 305 and cut the dura mater by driving the head portion 303 along the cutting direction such that the dura mater slides down the elevator 305 and towards the blade 30 where the dura mater has been cut.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An apparatus, comprising:
a scalpel housing defining a handle and a shield storage slot, the scalpel housing terminating in a head portion, wherein a distal end of the head portion defines a tip configured for engagement with a blade;
a shield defining an elevator and a blade shield in association with the head portion of the scalpel housing; and
a rotator defined by the shield in engagement with a rotator receptacle defined by the head portion of the scalpel housing;
wherein the shield is operable for rotation in a clockwise or counterclockwise direction between a recessed position in engagement with the shield storage slot of the scalpel housing and an engaged position such that the blade shield engages with the head portion of the scalpel housing and the elevator is positioned in distal relation to the tip;
wherein the rotator receptacle comprises:
a horizontal slot configured to receive the rotator of the shield
wherein the rotator receptacle comprises:
a post formed within the horizontal slot.

2. The apparatus of claim 1, wherein the shield further comprises:
a tip lock configured for engagement with the tip of the scalpel housing when the scalpel housing is in the engaged position, wherein the tip lock defines an elongated semicircular recess for engagement with the tip.

3. The apparatus of claim 2, wherein the tip lock further comprises:
a tip lock wall defined along a lateral edge of the tip lock.

4. The apparatus of claim 1, wherein the rotator comprises:
a longitudinal portion in communication with a circular portion; and
a latitudinal portion in communication with the circular portion, wherein the latitudinal portion is oriented in perpendicular relation to the longitudinal portion;
wherein the rotator is configured for insertion into the horizontal slot such that the post of the horizontal slot slides through the longitudinal portion and is disposed within the circular portion such that the rotator is operable for rotation between the recessed position and the engaged position; and
wherein the rotator is locked in the engaged position by driving the rotator in a lateral direction that causes the post to slide out of the circular portion and engage the latitudinal portion.

5. The apparatus of claim 1, wherein the head portion of the scalpel housing further comprises:
an upper surface defined proximal to the tip and configured for engagement with the blade shield of the shield; and
a blade receptacle configured for engagement with a blade.

6. The apparatus of claim 5, wherein the blade shield comprises:

an indentation defined along a lateral side of the shield for engagement with a blade while in the engaged position; and a brim defined directly above the indentation in a direction of elongation of the shield for engagement with the upper surface of the head portion of the scalpel housing when the rotator is in the engaged position;

wherein the blade shield is operable to prevent a blade from contacting tissue when the rotator is in the engaged position.

7. The apparatus of claim 1, wherein the shield storage slot comprises:
   a channel in communication with the rotator receptacle for engagement with the shield in the recessed position; and
   a tip slot in communication with the channel for engagement with the elevator of the shield in the recessed position.

8. The apparatus of claim 1, further comprising:
   a handle gripping portion defined along a handle surface of the handle of the scalpel housing; and
   a rotator gripping portion defined along an outer surface of the rotator of the shield.

9. The apparatus of claim 1, wherein an obtuse angle is defined between a direction of elongation of the shield and a direction of elongation of the elevator.

10. The apparatus of claim 9, wherein the elevator comprises an elevator ramp configured for engagement with a cutting edge of a blade while in the engaged position.

11. An apparatus, comprising:
    a scalpel housing defining a handle and a shield storage slot, the scalpel housing terminating in a head portion, wherein a distal end of the head portion defines a tip configured for engagement with a blade;
    a shield defining an elevator and a blade shield in association with the head portion of the scalpel housing; and
    a rotator defined by the shield in engagement with a rotator receptacle defined by the head portion of the scalpel housing;
    wherein the shield is operable for rotation in a clockwise or counterclockwise direction between a recessed position in engagement with the shield storage slot of the scalpel housing and an engaged position such that the blade shield engages with the head portion of the scalpel housing and the elevator is positioned in distal relation to the tip;
    wherein the rotator receptacle comprises:
      a horizontal slot configured to receive the rotator of the shield,
      wherein the rotator receptacle comprises a circular well formed within the horizontal slot of the rotator receptacle,
      and wherein the rotator comprises a rotator post configured for engagement with the circular well.

12. A shield for a dura elevating and cutting apparatus, comprising:
    a stem having a proximal end and a distal end;
    a rotator defined at the proximal end of the stem and configured for engagement with a rotator receptacle of a scalpel housing of the dura elevating and cutting apparatus;
    an elevator defined at the distal end of the stem; and
    a blade shield defined along a midsection of the stem and comprising a tip lock;
    wherein the stem is configured for engagement with a shield storage slot of the scalpel housing in a recessed position and the blade shield is configured for engagement with a head portion of the scalpel housing in an engaged position; and
    wherein the rotator is rotatable in a clockwise or counterclockwise direction between the recessed position and the engaged position.

13. The shield of claim 12, wherein the elevator terminates at a point and wherein an obtuse angle is defined between a direction of elongation of the stem and a direction of elongation of the elevator.

14. The shield of claim 12, further comprising:
    an elongated semicircular recess defined by the tip lock and configured for engagement with the tip of the scalpel housing when the shield is in the engaged position;
    an indentation defined by the blade shield along a lateral side of the stem for engagement with a blade when the shield is in the engaged position; and
    a brim defined by the blade shield and located directly above the indentation in a direction of elongation of the stem for engagement with the head portion of the scalpel housing when the shield is in the engaged position;
    wherein the blade shield prevents a blade from contacting tissue when in the engaged position.

15. The shield of claim 12, wherein the rotator further comprises:
    a longitudinal portion in communication with a circular portion; and
    a latitudinal portion in communication with the circular portion, wherein the latitudinal portion is oriented perpendicular to the longitudinal portion;
    wherein the rotator is configured to be inserted into a horizontal slot of the scalpel housing such that a post defined within the horizontal slot slides through the longitudinal portion and is disposed within the circular portion such that the rotator is operable for rotation between the recessed position and the engaged position; and
    wherein the rotator is locked in the engaged position by driving the rotator in a lateral direction such that the post slides out of the circular portion and engages within the latitudinal portion.

16. A method, comprising:
    inserting a rotator of a shield into a rotator receptacle of a scalpel housing, wherein the rotator comprises a longitudinal portion in communication with a circular portion and a latitudinal portion oriented in perpendicular relation to the longitudinal portion and in communication with the circular portion such that a post defined within the rotator receptacle slides through the longitudinal portion and is disposed within the circular portion;
    rotating the rotator in a clockwise or counterclockwise direction such that a direction of elongation of the shield is aligned with a direction of elongation of the scalpel housing; and
    driving the rotator in a lateral direction relative to the scalpel housing such that the post of the rotator receptacle engages within the latitudinal portion.

* * * * *